United States Patent
Darling, III et al.

(10) Patent No.: US 7,147,172 B2
(45) Date of Patent: Dec. 12, 2006

(54) PERSONAL DECONTAMINATION APPARATUS AND METHOD

(76) Inventors: Charles W. Darling, III, 6 Wells La., Hampton Bays, NY (US) 11946; John Mizzi, 30 Cramer Rd., Poughkeepsie, NY (US) 12603

(*) Notice: Subject to any disclaimer, the term of this patent is extended or adjusted under 35 U.S.C. 154(b) by 168 days.

(21) Appl. No.: 10/963,493

(22) Filed: Oct. 12, 2004

(65) Prior Publication Data

US 2006/0076433 A1  Apr. 13, 2006

(51) Int. Cl.
*A62C 13/62* (2006.01)

(52) U.S. Cl. ............... 239/302; 239/356; 239/359; 239/372; 239/373; 239/379; 239/366; 239/360; 222/5; 222/83; 222/89; 222/399

(58) Field of Classification Search ........ 239/356–379; 222/80–89, 386–399, 631, 633, 334; 169/85
See application file for complete search history.

(56) References Cited

U.S. PATENT DOCUMENTS

| | | | |
|---|---|---|---|
| 2,462,752 A | 2/1949 | Kotches | 229/84 |
| 2,562,294 A | 7/1951 | Cahenzli | 285/157 |
| 2,562,415 A | 7/1951 | Chase | 299/84 |
| 2,613,994 A | 10/1952 | Peters | 299/84 |
| 2,680,044 A | 6/1954 | Smith | 299/84 |
| 2,758,877 A | 8/1956 | Gleason | 299/84 |
| 2,800,313 A | 7/1957 | Targosh | 261/18 |
| 3,040,991 A * | 6/1962 | Fedit | 239/304 |
| 3,446,438 A | 5/1969 | Watson | 239/312 |
| 4,027,822 A | 6/1977 | Usher | |
| 4,121,773 A | 10/1978 | Headen | 239/317 |
| 4,266,813 A | 5/1981 | Oliver | 285/12 |
| 4,310,108 A * | 1/1982 | Motoyama et al. | 222/396 |
| 4,664,299 A * | 5/1987 | Goncalves | 222/327 |
| 5,008,011 A | 4/1991 | Underwood | 210/232 |
| 5,010,907 A | 4/1991 | Henson | 134/94 |
| 5,178,181 A | 1/1993 | Craig | 137/268 |
| 5,236,390 A | 8/1993 | Young | 454/95 |
| 5,356,076 A | 10/1994 | Bishop | 239/311 |
| 5,405,051 A * | 4/1995 | Miskell | 222/23 |
| 5,562,248 A | 10/1996 | Khalifka | 239/316 |
| 5,718,377 A | 2/1998 | Tedders | 239/8 |
| 5,795,471 A | 8/1998 | Naito | 210/223 |
| 5,878,915 A * | 3/1999 | Gordon et al. | 222/82 |
| 6,096,197 A | 8/2000 | Hughes | 210/94 |
| 6,182,911 B1 | 2/2001 | Hanks et al. | |
| 6,186,988 B1 | 2/2001 | Sabacinski | 604/289 |

(Continued)

OTHER PUBLICATIONS

PCT Search Report and Written Opinion, Applicant Charles W. Darling III, PCT/US2004/034118 dated Dec. 13, 2005, 10 pages.

(Continued)

*Primary Examiner*—Eric Keasel
*Assistant Examiner*—Trevor McGraw
(74) *Attorney, Agent, or Firm*—Alfred M. Walker (57) ABSTRACT

A personal decontamination apparatus includes an adapter valve attachable to a water source for mixing water with a concentrated decontamination fluid for rapid detoxifying washing of the skin of a user exposed to toxic chemical, biological or nuclear radioactive substances.

11 Claims, 10 Drawing Sheets

U.S. PATENT DOCUMENTS

| | | | |
|---|---|---|---|
| 6,395,172 B1 | 5/2002 | Koike | 210/282 |
| 6,446,277 B1 | 9/2002 | Blomet | |
| 6,485,683 B1 | 11/2002 | Walles | 422/4 |
| 6,537,455 B1 | 3/2003 | Farley | 210/251 |
| 6,769,572 B1 * | 8/2004 | Cullotta | 222/5 |
| 2001/0023900 A1 | 9/2001 | Stewart et al. | |
| 2003/0034051 A1 | 2/2003 | Barger | 134/10 |
| 2003/0038182 A1 | 2/2003 | Timmes et al. | |
| 2004/0083545 A1 | 5/2004 | Hudson | |

OTHER PUBLICATIONS

Block; Seymour S. ed. Disinfection, Sterilization, and Preservation, 1983, "In Medicine and allied Sciences", pp. 178-179.

Miracle Gro Scotts Company, "Miracle- Gro Product Guide", 2003, 2 page website advertisement.

Henry L.Stimpson Center, "Frequently Asked Questions; Personal Protection & Chemical or Biological Terrorism", 2002, 6 pages.

* cited by examiner

PERSONAL DECONTAMINATION APPARATUS AND METHOD

FIELD OF THE INVENTION

The present invention relates to personal devices for rapid decontamination of persons exposed to toxic substances.

BACKGROUND OF THE INVENTION

Weapons of mass destruction (WMD) may take the form of chemical, biological, or nuclear agents. Although people in the immediate vicinity of such a release will most likely succumb to the lethal doses inhaled or perhaps blast effects, others more remote to the source of contaminant (perhaps 95% of all those contaminated) will be affected by agents which are substantially diluted by air. This airborne "smog" can be lethal if particles remain on exposed skin for a substantial period through transdermal absorption. However, if the contaminants are washed off the skin quickly with a flood of water, most people will survive. If a strong shower with ample flow is not available, a smaller quantity of water with a decontaminant solution can be just as effective. For many agents, a weak solution of 5% household chlorine (bleach) is an effective decontaminant.

OBJECTS OF THE INVENTION

It is therefore an object of the present invention to provide personal hand-held or portable shower-mounted decontamination devices, or other devices temporarily attachable to sources of water, for rapid topical application of cleansing decontamination wash to the skin of persons exposed to toxic substances.

SUMMARY OF THE INVENTION

In keeping with these objects and others which may become apparent, the present invention includes an adapter valve which can be attached to a fluid source for rapid disinfecting of persons exposed to products of weapons of mass destruction (WMD). The adapter can be a canister which mixes fresh water from a shower or other water source, such as a hose spigot, with chemical rescue products for rapid detoxification of the skin, such as a mixture of 5% Clorox and water. The source can also be portable containers, such as a large 50 gallon field water bag used in military applications for portable showers. The items can be in a kit including canisters of materials for detoxifying persons exposed to biological, chemical or nuclear weapons of mass destruction. The device can be a self drenching hand-held pressurized pistol with a predetermined amount of water and a treatment solution in a second canister.

This invention provides an apparatus that can be used with household pressurized water or even in the absence of such a water source to wash the exposed skin with a decontamination solution. The first embodiment is meant to be connected to household pressurized water. It includes a special connector with two female threaded receptacles sized so as to connect either to an outdoor hose spigot or to a standard showerhead connection. The connector has a two-way valve to select the desired receptacle as well as a backflow preventer (to protect the water supply from contamination) and a quick-connect coupling. The coupling mates with a short length of flexible hose with quick-connect mating couplings at both ends. The third major part of this embodiment is a liquid dispenser which is designed to mix a concentrated liquid with pressurized water for dilution and spraying through a nozzle. This can be a venturi type of apparatus or other mixing type similar to those used to mix and dispense liquid fertilizer (such as the MIRACLE GRO® dispenser) but adapted to provide the proper degree of dilution for this application. This dispenser has a quick-connect coupling identical to that on the special connector. To use in an emergency, the liquid container on the dispenser is quickly filled with the concentrated decontamination solution. Preferably, the solution is provided from a date-stamped sealed container with long shelf life such as three years. One end of the hose is plugged into it. The special connector is then screwed into a hose spigot or a shower connector (after the shower head is screwed off), and the selector valve is properly set. The free end of the hose is plugged into the special connector and the water supply is turned on. At a campsite where no running water is available, the special connector can be screwed into a threaded male outlet connected to an elevated water bag or tank used as a portable shower.

In the absence of any pressurized water source, the second embodiment of this invention includes an aerosol dispenser. The aerosol dispenser has a dated amount of a decontamination substance, such as for example, a water and five (5%) chlorine mixture or other appropriate topical cleansing decontamination substance. The aerosol dispenser has a long shelf life, such as for example, three years, so that it will still be active where needed. The aerosol container may have the cleansing decontamination substance factory installed and sealed, or it may be a refillable aerosol dispenser with two chambers, one for a liter or more of water and a second smaller chamber for the concentrated decontamination solution. The propellant used may be from a canister, or it may be compressed air manually supplied through an efficient ergonomically designed compressor. The compressor may be trigger operable, such as with an asymmetric dual bellows type operated by rapidly squeezing an operating bar incorporated into the handle. This compressor is designed to rapidly pressurize an unpressurized chamber and then raise the internal pressure to a high terminal level. Prior art compressors were a compromise between these two goals. Once pressurized, a dispensing valve is used to discharge pressurized water through a venturi which aspirates decontamination concentrate and mixes it with the water stream before it exits the spray nozzle. When the pressure is somewhat depleted after steadily discharging solution for at least 30 seconds, a few more strokes of the operating bar will restore operating pressure for further spraying.

The third embodiment is a long-term storage aerosol dispenser using a preferably date stamped, hermetically sealed container of a cleansing decontamination wash substance such as, for example, a premixed user strength decontamination solution and a separate hermetically sealed pressurized propellant cartridge. Normal aerosol dispensers have a design-acceptable leakage rate and lack the propellant energy to dispense a large amount of liquid at a fast rate. This aerosol dispenser uses a fast rate discharge valve/nozzle and a small sealed high-strength cartridge of high energy propellant such as liquified carbon dioxide. A second version of this embodiment uses a larger container (such as 3–5 liters) and a comparably larger propellant tank. Since such a version would be unwieldy to operate like an ordinary aerosol dispenser, it is meant to be placed on the floor and used with a hose-attached dispensing valve/nozzle. The internal technology of this version is identical to that of the smaller version described. A key feature of this embodiment is the bellows section of the hermetically sealed liquid container which is collapsed via a screw top to pierce the container top to permit liquid discharge and then to pierce the pressurized propellant tank upon further turning.

The fourth embodiment describes a decontamination system that can be used in any venue where shower facilities are available. It can be used with normal domestic or institutional water supplies, or even in a field situation with showers fed by a gravity system using a flexible water bladder as supply. A venturi siphon adapter is introduced between the showerhead supply pipe and the showerhead by screwing it into the supply pipe and tightening with a wrench. This can be done in one or more bathrooms in a home, for example. This adapter is a chrome plated short length extension which does not alter the height of the showerhead appreciably and it blends in with normal bathroom plumbing. It is also compatible with the use of handheld shower wands by introducing the venturi adapter between the supply pipe and the source end of the flexible hose extension. In case of an emergency involving a WMD attack, a factory-filled, date stamped bottle of the proper decontamination fluid (chemical, biological, or radiological type) is simply plugged into the siphon port of the venturi siphon adapter with a "click". When water starts flowing through the showerhead, decontamination fluid will be drawn from the attached bottle and thoroughly mixed with the water flow. To disconnect the decontamination bottle, a release button on the side of the siphon port is pressed. The siphon port preferably has an automatic sealing quick connect/disconnect fitting which mates with a compatible fitting on top of the cap of the decontamination bottle.

BRIEF DESCRIPTION OF THE DRAWINGS

The present invention can best be understood in connection with the accompanying drawings. It is noted that the invention is not limited to the precise embodiments shown in drawings, in which.

DETAILED DESCRIPTION OF THE INVENTION

Figure 1:
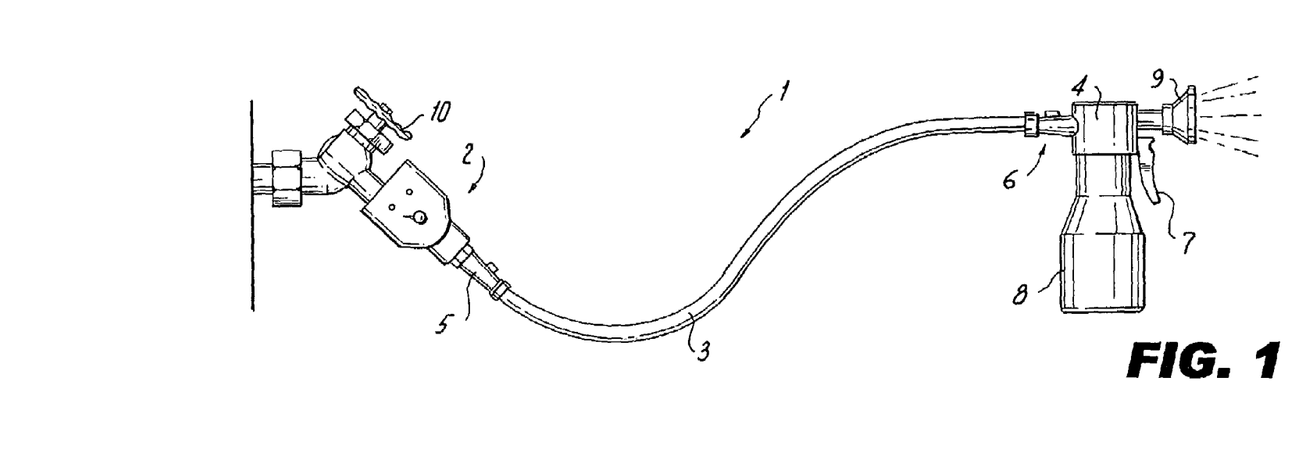
FIG. 1 is a Side elevation view of the first embodiment of this invention using a liquid dispenser hose-attached to a household supply of pressurized water for dispensing a cleansing decontamination treatment wash for treating victims exposed to toxic substances and/or hazardous materials.

FIG. 1 shows the first embodiment for a dispenser 1 of this invention which is meant to be connected to a supply of household pressurized water. Here hose spigot 10 is connected to special connector 2 which couples to hose 3 which terminates in decontamination spraying dispenser 4.

Figure 2:
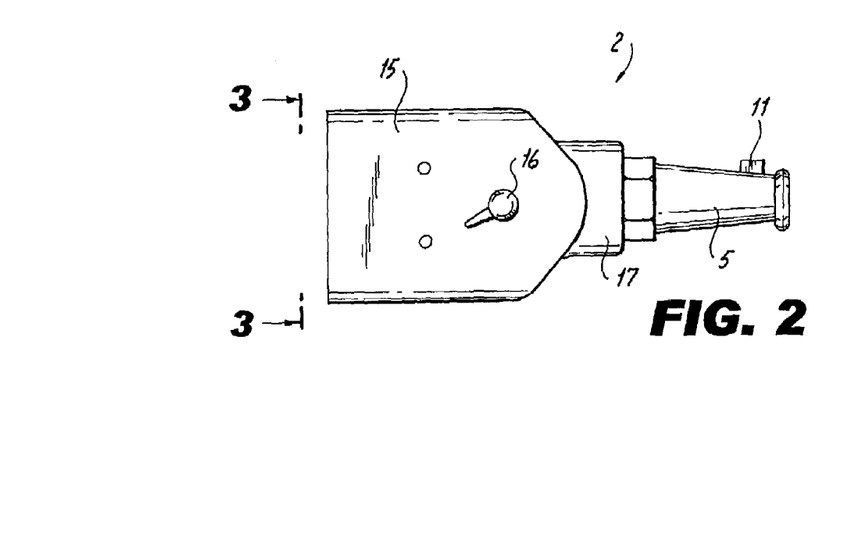
FIG. 2 is a Side elevational view of a special dual orifice connector used with the first embodiment shown in FIG. 1.
Figure 3:
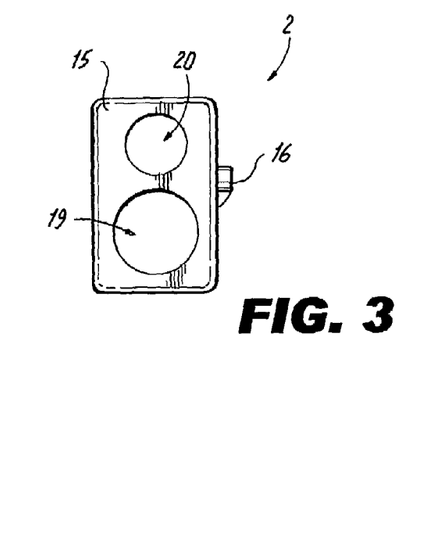
FIG. 3 is an End view of the connector shown in FIG. 2.

FIGS. 2 and 3 show closer views of special connector 2. Connector 2 has flattened housing 15 with hose coupling female threaded orifice 19 and smaller female threaded orifice 20 sized to couple with a shower head connector. Housing 15 also has a selector valve operated by knob 16 to couple the distal end to either orifice 19 or 20. Housing 17 contains a commercially available cartridge type backflow preventer. Quick disconnect coupling 5 with release button 11 completes special connector 2. The latter can be a straight through HFC 108-35 coupling from Colder Products Company of St. Paul, Minn. The offset placement of threaded orifices 19 and 20, along with the flattened configuration of special connector 2 permits reliable leak free attachment to hose or shower connectors with just hand applied torque. Elastomeric sealing washers (not shown) are embedded at the bottom of both coupling orifices. Spraying dispenser 4 draws concentrated decontamination fluid from reservoir 8 in the proper ratio to mix with water flowing through spray head 9 whenever discharge lever 7 is actuated. Preferably reservoir 8 is date stamped, with a long shelf life, such as, for example, three years. Quick disconnect coupling 6 is identical to coupling 5. Hose 3 is terminated in mating couplings such as straight through type HFC 228-35 also from Colder.

Figure 4:
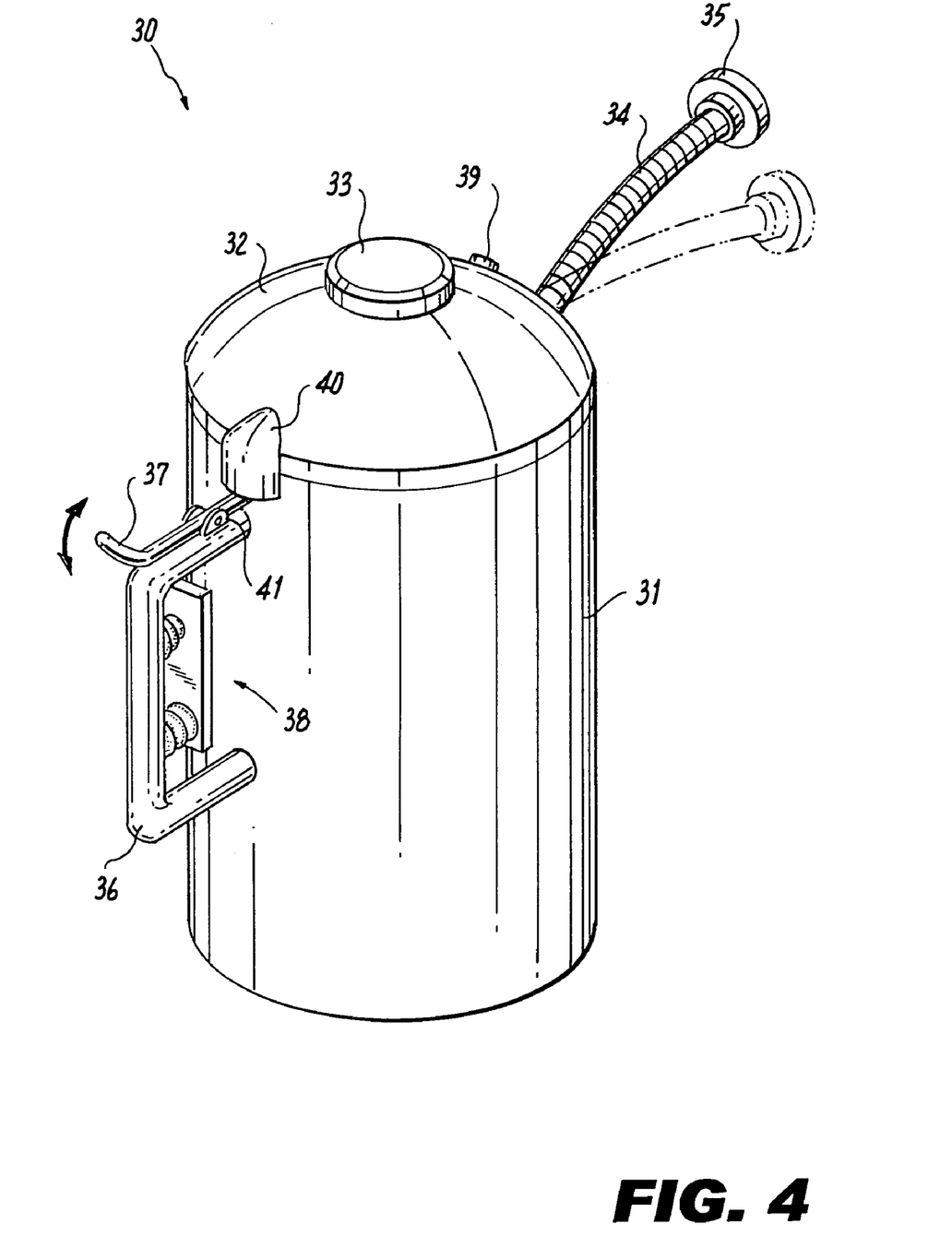
FIG. 4 is a Perspective view of a second embodiment of this invention, incorporating an aerosol dispenser using manually generated compressed air as the propellant for dispensing a cleansing decontamination treatment wash for treating victims exposed to toxic substances and/or hazardous materials.

FIG. 4 shows aerosol dispenser 30 which is the second embodiment of this invention used for decontamination in areas not adjacent to pressurized water supply. It includes housing 31, hollow handle 36, compressor assembly 38, cap assembly 32 and locking knob 33. Attached to handle 36 is a trigger mechanism, such as, for example, pivot 41 for thumb-operated discharge lever 37. Attached to cap assembly 32 is a fluid output, such as, for example, adjustable gooseneck 34 terminating in nozzle 35, discharge valve coupling cover 40 and inlet venting check valve 39.

Figure 5:
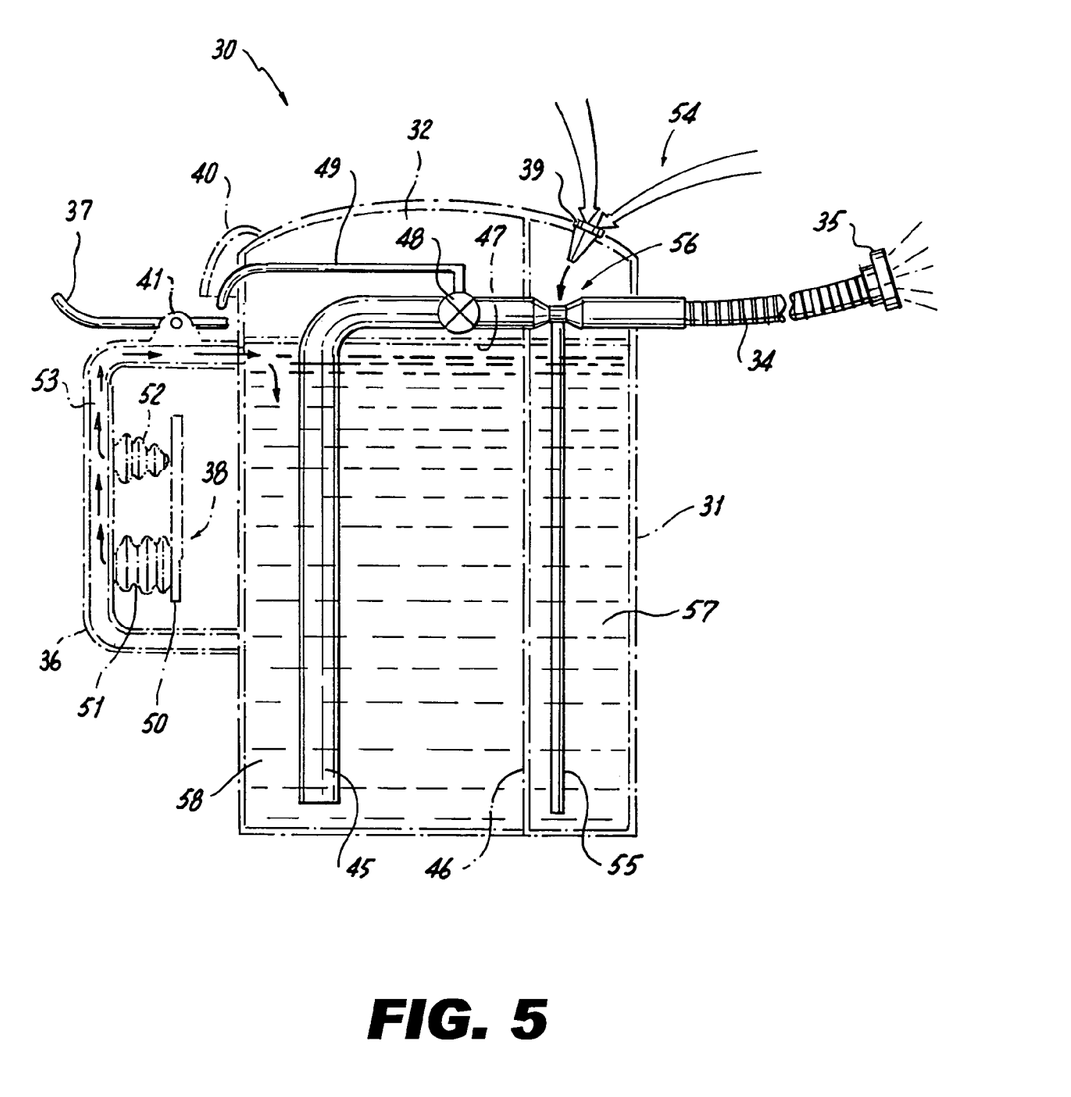
FIG. 5 is a Schematic side view in partial crossection of hydraulic and pneumatic components of the aerosol dispenser of FIG. 4.

The operation is best understood by reference to the schematic drawing of FIG. 5. Inside housing 31 are two separate compartments or chambers 57 and 58. Preferably one compartment is larger than the other compartment. The larger compartment or chamber 58 is filled with water leaving a small air space on top. The smaller compartment 57 is filled with concentrated decontamination fluid, preferably from a date stamped supply container with a long shelf life. Cap assembly 32 has dip tube 45 which leads to discharge valve 48 and venturi restriction 56 along with concentrate dip tube 55. Compartment 58 is sealed at the top at 47 and by side partition 46. Compartment 57 is vented to the atmosphere 54 via inlet check valve 39 (vacuum breaker). In this configuration, pressure at venturi 56 must be below atmospheric to draw concentrate from compartment 57. Alternatively, compartment 57 can be sealed to the atmosphere and check valve 39 is relocated to communicate pressure from chamber 58 to chamber 57 through partition 46 while still isolating the two liquids. A resizing of venturi 56 would be required to properly meter concentrate in the pressurized version of chamber 57. Manually operated compressor assembly 38 feeds compressed air for discharge of cleansing decontamination fluid. For example, compressor assembly 38 preferably incorporates large bellows 51, small tapered bellows 52 and coupling bar 50 feeds compressed air into hollow handle 36 which is then discharged into compartment 58 to be used as the aerosol propellant. Discharge valve actuator 49 couples with thumb operated discharge lever 37 when cap assembly 32 is locked atop housing 31.

Figures 6, 7:
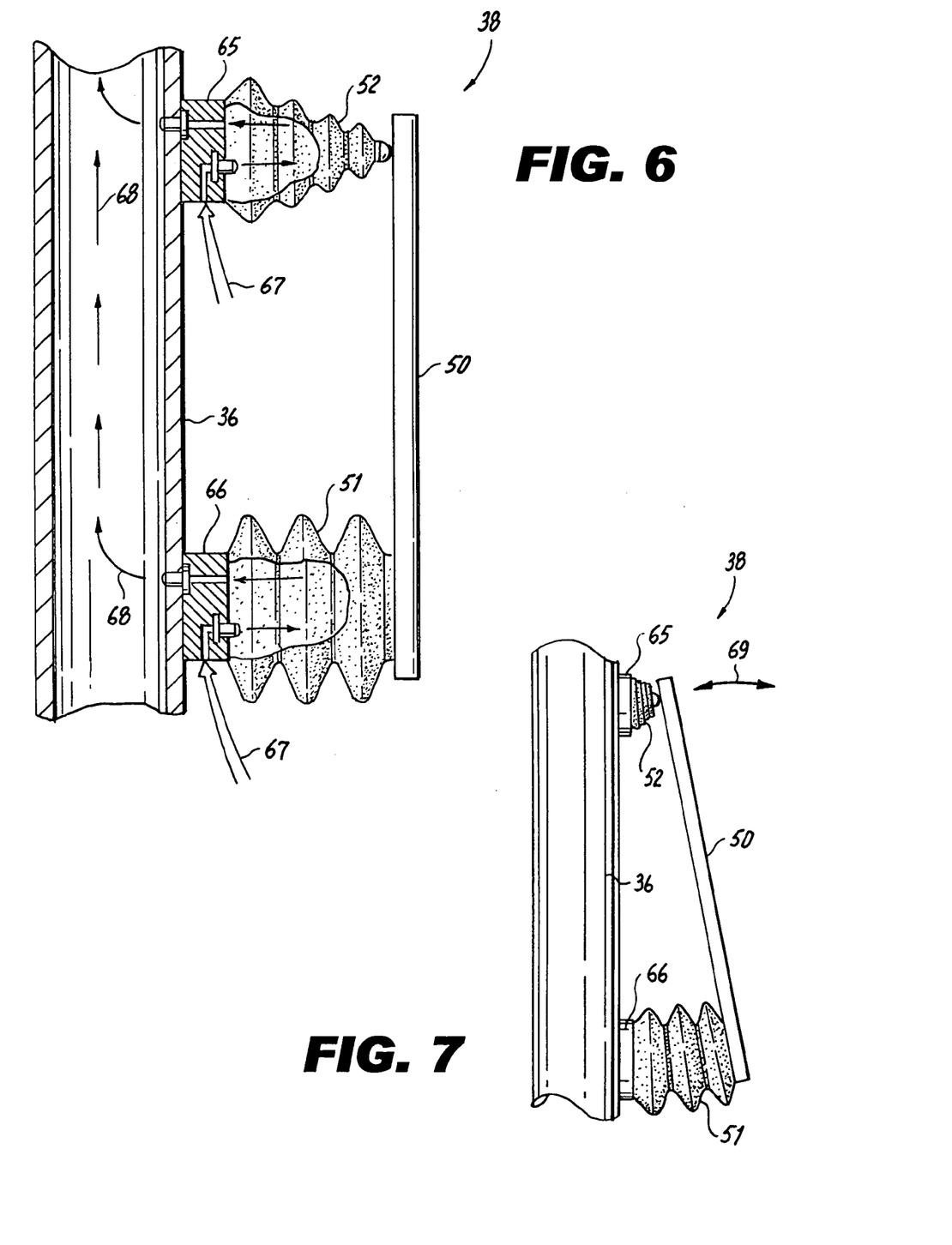
FIG. 6 is a Crossectional side view of an asymmetric dual bellows compressor used in the second embodiment of this invention shown in FIGS. 4 and 5.
FIG. 7 is a Side view illustration of the operation of the manual compressor of FIG. 6, shown with substantial back pressure.

The operation of ergonomically designed manual compressor assembly 38 is illustrated in FIGS. 6 and 7. This is an asymmetric dual bellows design which is efficient and specially designed to promote rapid pressure build-up of a chamber at low or atmospheric pressure as well as high terminal pressure (exceeding 50 psig). Large bellows 51 with valve block 66 draws in ambient air 67 through an inlet check valve on its expansion stroke and discharges compressed air 68 through an outlet check valve on its compression stroke into the hollow interior of handle 36. Similarly, smaller tapered bellows 52 with valve block 65 contributes compressed air to the interior of hollow handle 36. Both bellows operate in parallel and independently, rapidly building up pressure when bar 50 is squeezed repeatedly. At some point, depending on the squeezing force and back pressure communicated through hollow handle 36, it will be too difficult to squeeze large bellows 51.

However, as shown in FIG. 7, smaller tapered bellows 52 will still be squeezable and that end only of bar 50 will oscillate 69 pivoting on large bellows 51 which will act as a hinge in this phase of high pressure compression. The transition from parallel operation of both bellows to the single bellows operation is seamless and hardly apparent to the user. The bellows are made of blow molded polyproplyene or similar plastic resin.

A third embodiment of this invention is illustrated in FIGS. 8 through 10.

FIG. 8 shows a long-term storage special hand-held aerosol dispenser 80 with housing 81, discharge valve/nozzle 83, and activating twist cap 82. A frangible tamper evident tape wrap 96 is used to insure integrity of this emergency decontamination dispenser. As distinguished from ordinary aerosols, this is a zero leakage hermetically sealed dispenser designed for long term shelf life storage, rapid robust discharge, and ease of use. The user simply actuates the dispensing of fluid by twisting activator cap 82 several turns and then proceeds to dispense the pre-mixed proper concentration decontamination fluid by pressing discharge valve 83.

The side view crossection of FIG. 9 shows the preferable operating principle. A robust pressure resistant housing 81 has bellows type convolutions 87 formed in the top section. After all the internal components are mounted and housing 81 is filled with fluid 95, the top is hermetically sealed as by welding or soldering. A suitable non corroding material such as stainless steel, or alternatively a non-corroding coating (internally and externally) is used for housing 81. Dip tube 89 is attached to the center of the top of housing 81 with an elastomeric seal 88 at it top end. Support tube 93 is attached to the bottom of housing 81 and a propellant tank support housing with spring supports 92 is attached to its top end. High pressure propellant tank 90 which is hermetically sealed is thereby placed centrally over hollow piercing needle 91 rigidly attached and communicating to the interior of support tube 93. Piercing hollow needle 86 communicates with discharge valve 83 and is rigidly attached to activator cap 82. A ring of threads 84 which engage threads 85 on the inside of cap 82 is attached rigidly to the exterior of housing 81. It can be appreciated that by turning cap 82 thereby screwing it down relative to housing 81, first, the top of housing 81 is pierced by needle 86. There is no leakage since the interior of housing 81 is not pressurized at this point. Further turning of cap 82 will, in turn, seal hollow needle to elastomer seal 88 and then collapse the top of housing 81 thereby forcing tank 90 onto hollow needle 91 piercing its end and releasing propellant into tube 93 whereby it escapes into the interior of housing 81 through holes 94 thereby instantly pressurizing housing 81. A small 12 gram carbon dioxide tank as commonly used in pellet guns is sufficient to pressurize a one liter (or somewhat larger) aerosol dispenser 80.

A larger version 100 of this embodiment is illustrated in FIG. 10. A larger tank 101 (3 to 5 liters) is necked down at the top and accommodates a pressure release activator, such as, for example, a larger twist activator cap 102. The interior of the necked down portion is identical to the convoluted construction of FIG. 9. A larger propellant tank commensurate with the larger dispensing volume is used. The operation is the same as described in FIG. 9. In this version, a quick connect coupling with automatic shutoff 103 is attached to cap 102 in place of valve/nozzle 83 of FIG. 9. This can be an HFCD 108-35 from Colder Products. A mating coupling 107 attached to hose 104 will automatically open connector 103 when inserted. Coupling 107 can be a colder HFCD 228-35. Hose 104 attaches discharge valve/nozzle 105 operated via lever 106 at its other end.

While drawings 8–10 depict hermetically sealed hand-held aerosol dispensers useful for decontamination use, certain enhancements can make them more desirable. As shown, they represent a zero leakage design wherein the housing is unpressurized during storage and the propellant is isolated within in a separate high pressure tank; this is a very safe design. The pressure and volume of propellant is designed to be consistent with the volume of decontamination solution to be discharged, the strength of the liquid housing, and the amount of head space above the liquid as filled at the factory, where the dispenser is date stamped to indicate shelf life. The pressure will decrease somewhat as liquid is discharged.

Figures 8, 9, 10:
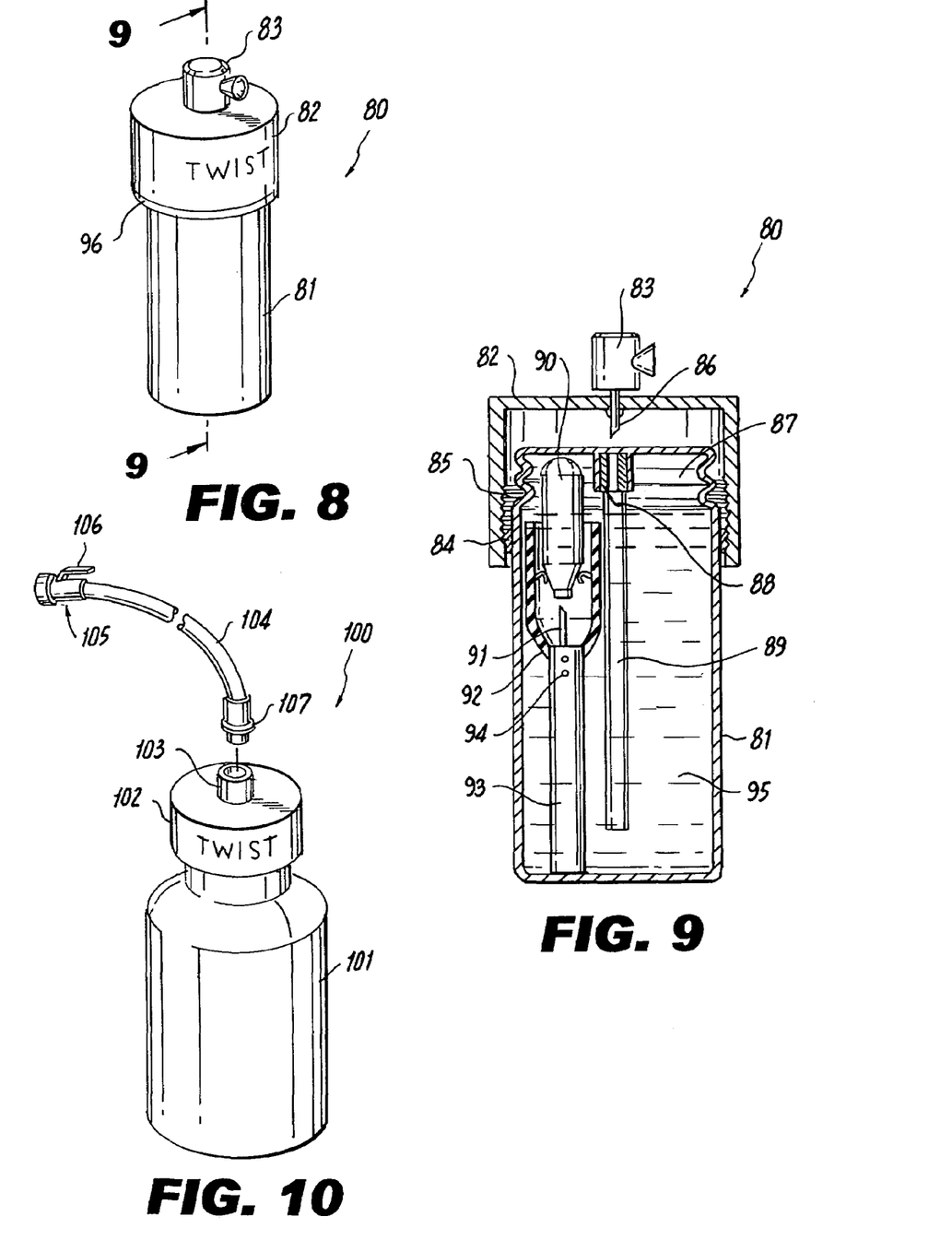
FIG. 8 is a Perspective view of a third embodiment of this invention for a hand-held hermetically sealed aerosol dispenser for dispensing a cleansing decontamination treatment wash for treating victims exposed to toxic substances and/or hazardous materials.
FIG. 9 is a Side crossectional view of the hand-held aerosol dispenser of FIG. 8.
FIG. 10 is a Perspective view of a large version of the hand-held aerosol dispenser of FIG. 9, shown using a hose-connected discharge valve/spray nozzle.

While FIGS. 8, 9 and 10 show various preferably twist cap activators, it is known that other button activated, lever activated or other pressure release mechanisms known to those skilled in the art may be employed.

Figure 11:
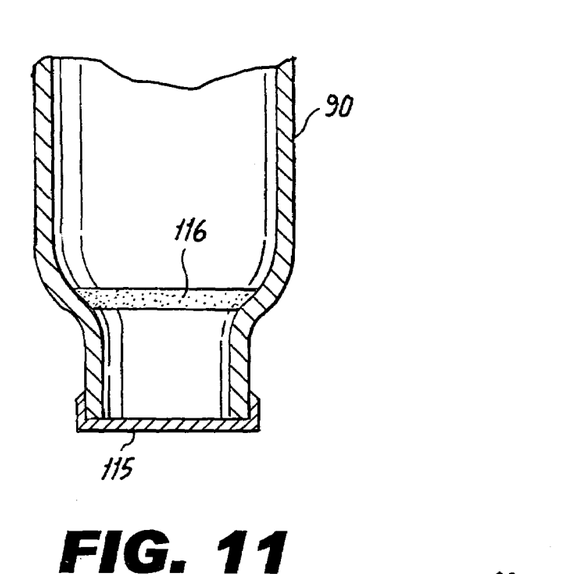
FIG. 11 is a Side crossectional detail view of a high pressure propellant tank of the hand-held aerosol dispenser of FIG. 9, showing the location of an outlet pressure regulator.
Figure 12:
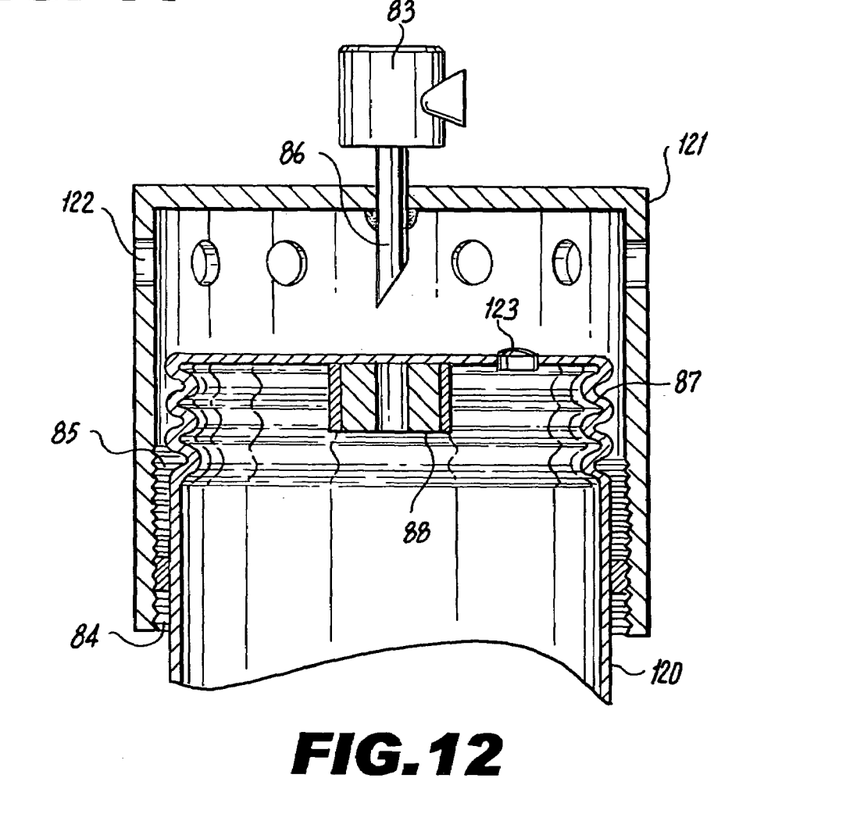
FIG. 12 is a Side crossectional detail view of an aerosol housing and cap with enhancement features for the hand-held aerosol dispenser shown in FIGS. 8 and 9.

The preferable enhancements shown in FIGS. 11 and 12 will optimize the amount of decontamination liquid in any given size dispenser and reduce the overall weight, in addition to providing fairly constant discharge pressure from full to empty. This is accomplished by the addition of discharge pressure regulator 116 which is installed within propellant tank 90 upstream of sealing cap 115 which is pierced by hollow needle 91 at activation (see FIG. 11). Pressure regulator 116 reseals tank 90 when the desired discharge pressure inside the liquid housing has been reached. As more liquid is dispensed, more propellant is metered into the housing to maintain pressure.

FIG. 12 shows the rest of the preferable enhancement features. Since housing 120 now receives a regulated pressure from propellant tank 90, it can now be fabricated from reduced gage material thereby reducing dispenser weight. Also, the head space at filling can be reduced since the only requirement is the minimum gas space at ambient pressure to permit easy actuation of these aerosol dispensers by collapsing the convoluted top section. As these two changes could represent an explosion hazard in case of regulator 116 failure, a safety device such as a welded rupture disc 123 is added to the top of housing 120 along with a series of vent holes 122 in activation cap 121. In this way, propellant tank 90 can be smaller and with higher pressure for a given dispenser size thereby using less internal volume (this permits more decontamination liquid to be housed).

Figure 13:
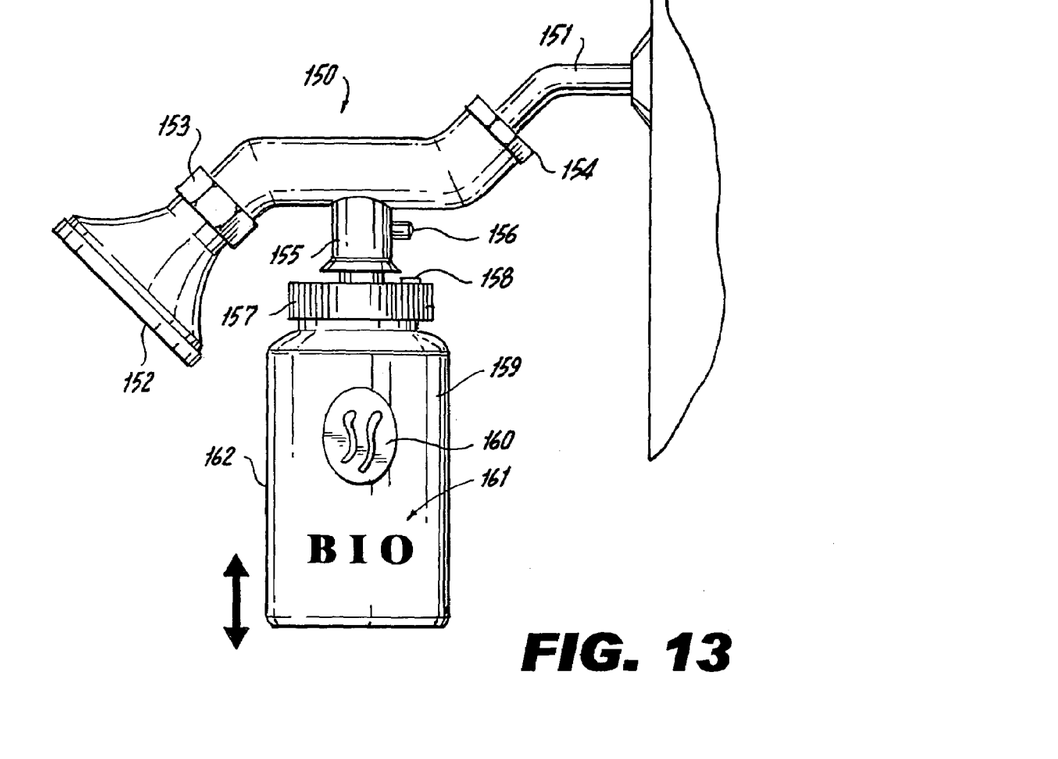
FIG. 13 is a Side elevational view of a fourth embodiment for a wall-mounted shower head adapter dispenser, shown with a venturi siphon adapter with an attached decontamination fluid bottle for dispensing a treatment wash for victims exposed to toxic substances and/or hazardous materials.

FIG. 13 shows a side view of the fourth embodiment of this invention for use with shower fixtures. A permanently installed fluid direction controller such as venturi siphon adapter 150, is preferably plumbed between supply pipe 151 and showerhead 152. A decontamination bottle 162 is shown attached to siphon port 155 with release button 156 on the side. A fastener, such as lock nut 154 with internal o-ring is used to lock and seal venturi adapter 150 in place once it threaded onto pipe 151 and in the proper position with siphon port 155 vertical. Fastener 153, such as a nut, part of showerhead 152, is screwed onto the end of venturi adapter 150. Bottle 162 is factory-filled with biological weapon decontamination fluid in this illustration as indicated by the large "BIO" label and the non-verbal international symbol 160 for this type of contamination emblazoned on its container 159. Similar bottles would be labeled "CHEM" or "RAD" to indicate chemical or radiological contamination respectively; the appropriate international symbol 160 would also be displayed and bottle 162 is date stamped to indicate shelf life. Bottle cap 157 has vent seal 158 which allows ambient air to enter container 159 thereby preventing vapor lock.

Figure 14:
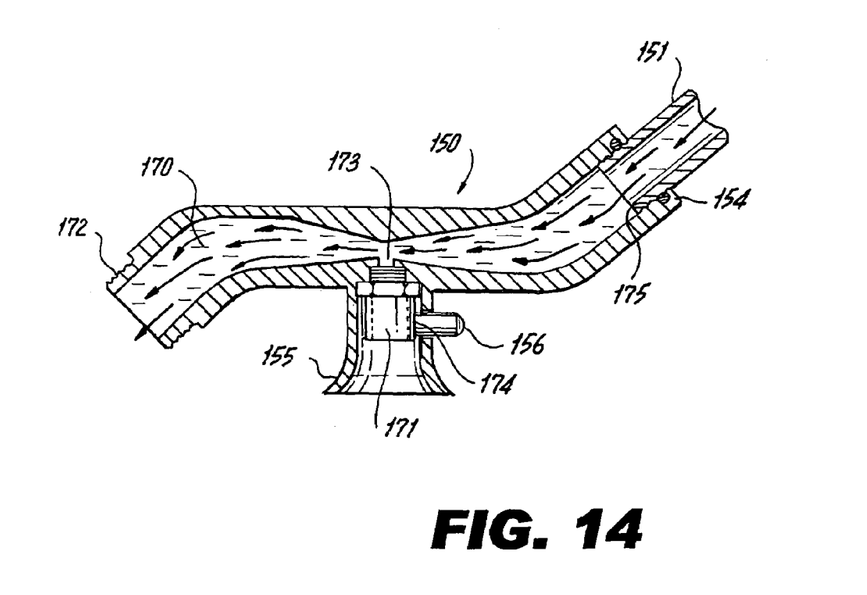
FIG. 14 is a Side central crossectional view the venturi siphon adapter for the wall mounted shower head adapter dispenser of FIG. 13.

FIG. 14 is a crossection view of the internals of venturi siphon adapter 150. The gentle curvature of the internal water channels 170 reduces pressure loss. The diameter reduction at siphon tap 173 is the minimum that will insure effective draw and mixing of decontamination fluid even at reduced flow rates so as to reduce overall pressure reduction at showerhead 152. The rate at which fluid is drawn from bottle 162 is related to the water flow rate thereby insuring a relatively constant effluent decontamination fluid concentration. Siphon port 155 is shaped to guide the mating member from bottle 162 into coupler 171 with side latch release 174. Button 156 with internal spring biasing it outward, will transmit a force to latch release 174 when pressed. This will release bottle 162. Note the simplicity of venturi siphon adapter 150 with no valves or adjustment levers. It will start drawing decontamination fluid as long as a non-empty bottle 162 is attached and water is flowing through showerhead 152. Showerhead 152 preferably screws onto threads 172.

Other fluid direction controls may be employed for mixing water from source pipe 151 with decontamination fluid from bottle 162.

Figure 15:
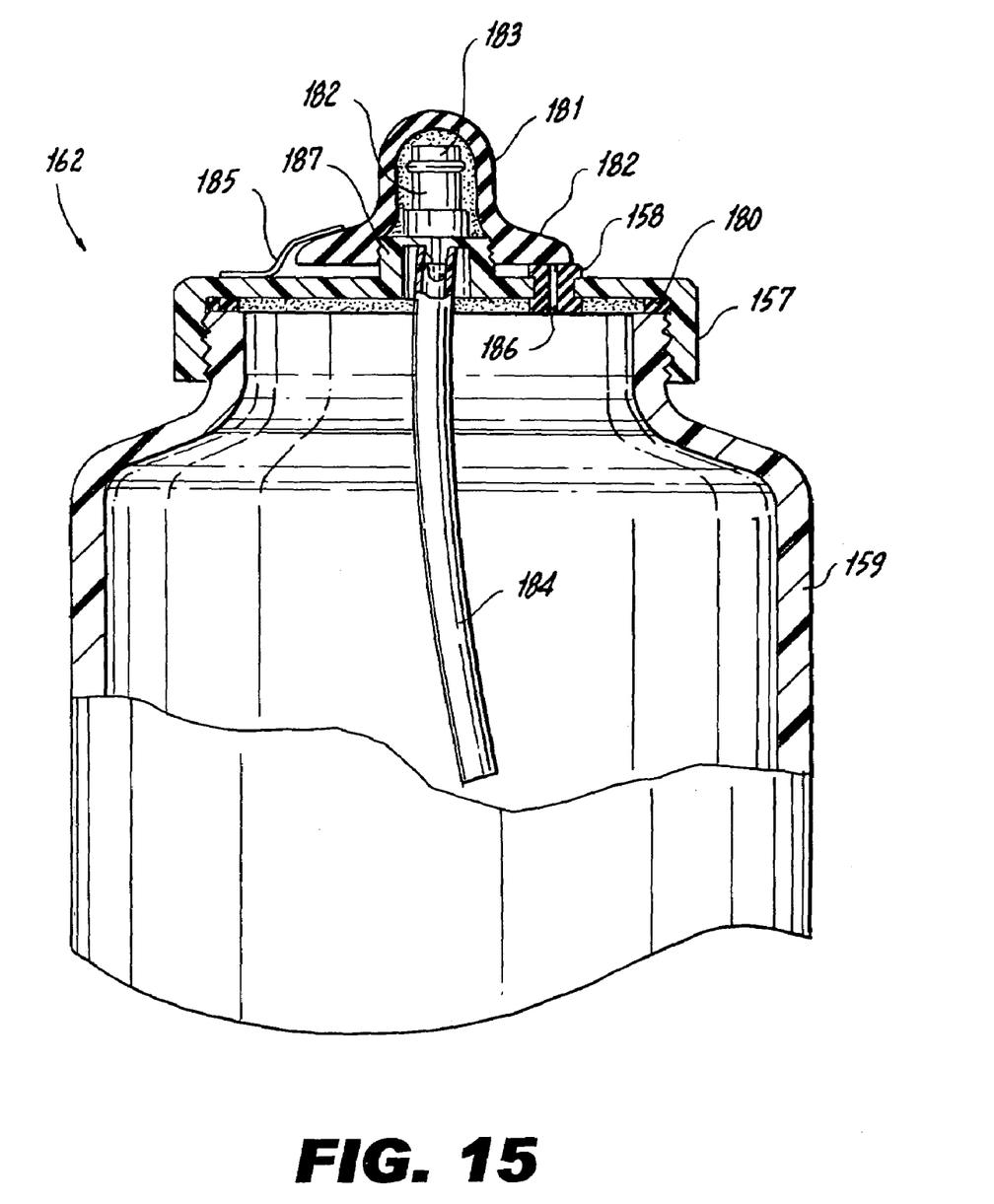
FIG. 15 is a Side central crossectional detail view of a top portion of the decontamination bottle of the fourth embodiment of this invention shown in FIG. 14.

FIG. 15 is a side central crossection of the top portion of bottle 162. Bottle cap 157 is shown threaded onto container 159 with elastomeric seal 180. Adhesive can be used on these threads as the user need not gain access to the inside of container 159. Alternatively, cap 157 can be simply adhesively bonded to container 159 without the use of threads. Cap protrusion 187 is threaded on its external surface to receive protective cap 181 with base flange 182. Cap 181 protects quick connect/disconnect member 182 with sealing o-ring 183. Member 182 enters coupler 171 which is part of venturi siphon adapter 150 to click-lock together providing a liquid conduit for decontamination fluid and also providing a mechanical means to support the weight of bottle 162 from adapter 150. Member 182 is adhesively or otherwise attached to protrusion 187 and is coupled to semi-rigid dip tube 184 which reaches to the bottom of container 159. Member 182 can be part number PMCD 22-01-12 with integral shutoff while coupler 171 can be part number PMCD 10-02-12 also with integral shutoff both from Colder Products Company. Note that flange 182 seals orifice 186 in elastomeric vent seal 158 when it is screwed down; this seals bottle 162 from environmental contamination. The user unscrews cap 181 before coupling bottle 162 with adapter 150; this action unseals vent orifice 186 and also breaks frangible tamper evident tape 185.

FIGS. 16–19 show various dispensers for rapid dispensing of cleansing decontamination washes, for topical treatment of skin exposed to toxic substances, such as nuclear, biological or chemical substances. Rapid cleansing with a treatment wash reduces the effects of topical exposure to the toxic substances, and/or hazardous materials and prevents grave internal burns or other damage to internal organs.

In order to achieve the rapid cleansing, the various dispensers shown in FIGS. 16–19 may be used in different situations.

Figure 16:
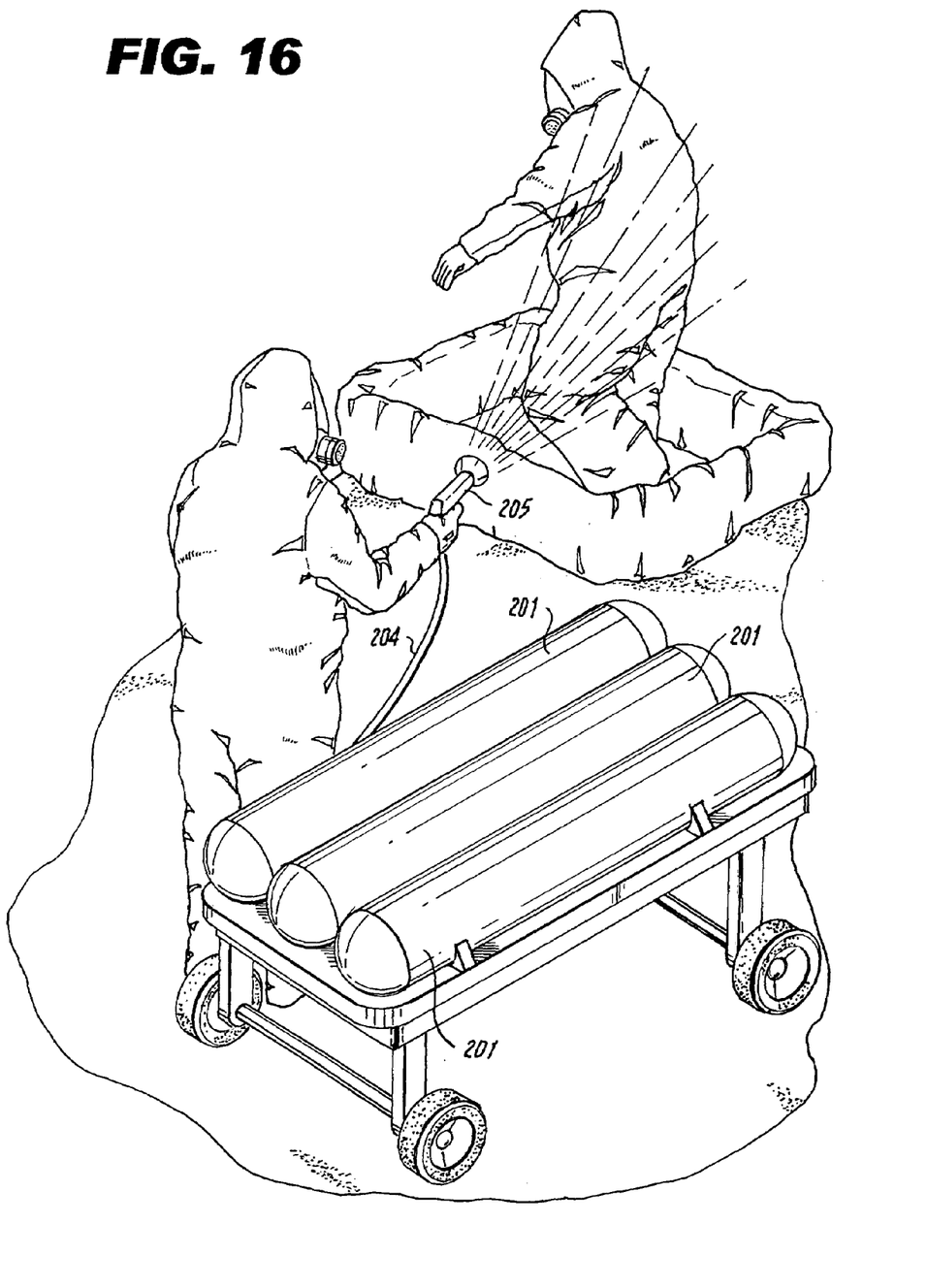
FIG. 16 is a Perspective view of a field treatment hose dispenser for rapid cleansing decontamination treatment washing of a victim exposed to toxic substances and/or hazardous materials.

For example, FIG. 16 shows a decontamination treatment wash being rapidly dispensed from dispenser 205, connected by flexible hose 204 to one or more fluid sources, such as portable fluid bags or canisters 201 containing the appropriate decontamination treatment wash mixture dispensed therefrom.

Figure 17:
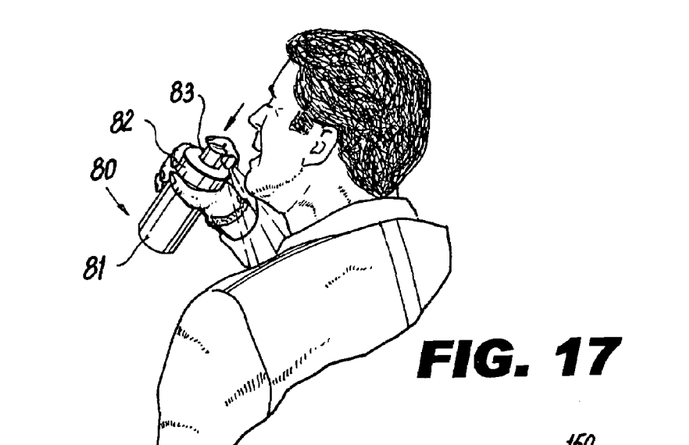
FIG. 17 is a Perspective view of a person using a hand held aerosol dispenser dispensing a cleansing decontamination treatment wash for exposure toxic substances and/or hazardous materials.

However, where mass exposure to toxic substances makes it difficult to get many victims to field treatment facilities, such as that shown in FIG. 16, as shown in FIG. 17, hermetically sealed hand-held dispensers 80, having hand-held housing 81, twist-cap 82 and discharge valve 83, such as shown in FIGS. 8 and 9, may be carried by a person, so that the person can rapidly self-cleanse his or her skin as soon as the person is exposed to toxic substances, such as in a rescue-inaccessible environment. For example, in a mass transit rail vehicle or in an entertainment or sports stadium, it may not be feasible to mobilize and collectively wash hundreds or thousands of persons exposed to toxic substances and/or hazardous materials. In such situations, if carried in a pocket or handbag, a portable hand-held aerosol dispenser, such as aerosol dispenser 80, may be used. Each person exposed to the toxic substances and/or hazardous materials can activate the hand-held dispenser and rapidly decontaminate the skin by spraying decontamination fluid onto exposed areas of the skin.

Figures 18, 19:
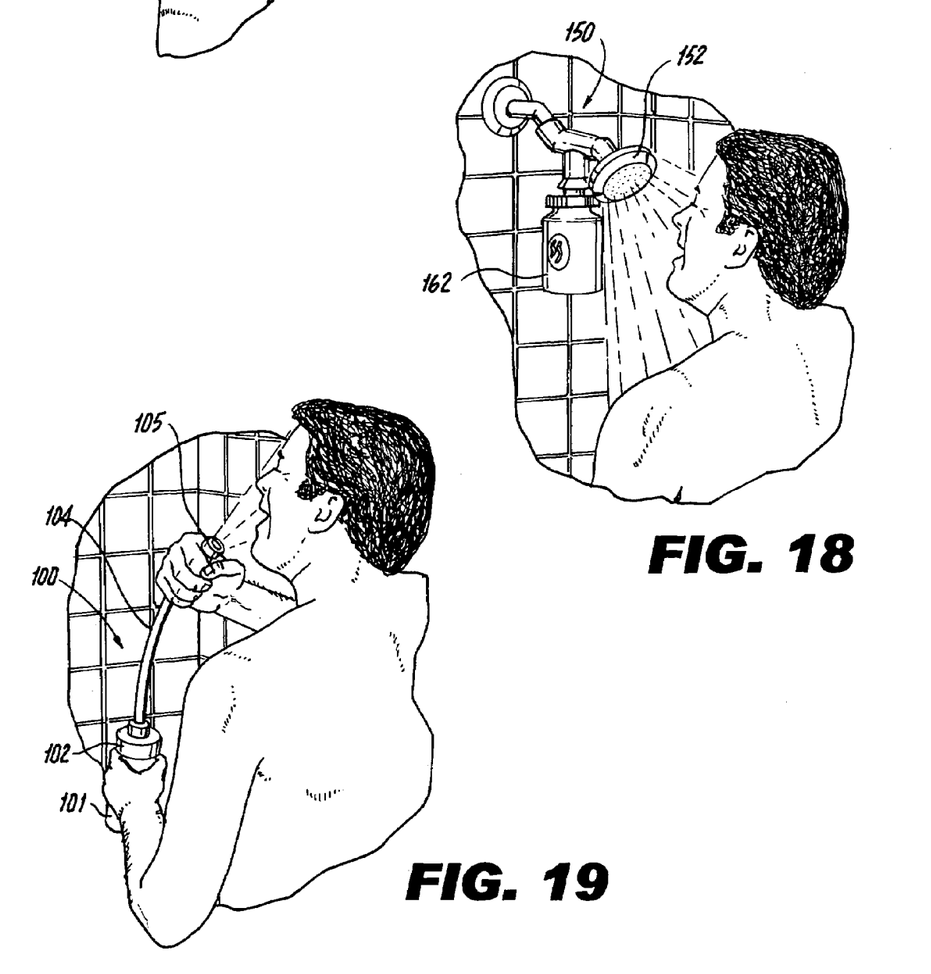
FIG. 18 is a Perspective view of a person using a wall mounted domestic shower adapter with a canister for dispensing a rapid cleansing decontamination treatment wash for exposure to toxic substances and/or hazardous materials.
FIG. 19 is a Perspective view showing a person using another hand-held dispenser with a canister and hose for dispensing a rapid cleansing decontamination treatment wash for exposure to toxic substances and/or hazardous materials.

As shown in FIG. 18, residential or institutional shower heads 152 can be adapted with connectable adapters 150 to treat victims with mixtures made of water and cleansing decontamination treatment washes substances, such as chlorine, provided in canisters 162, The water is provided from the conventional shower water source and mixes with the decontamination fluid in adapter 150.

FIG. 19 shows a different hand-held dispenser 100 with twist lock cap 102. flexible hose 104 and spray discharge nozzle 105. Other configurations for dispensing a controlled pressurized amount of cleansing decontamination treatment wash from a container through an outlet may be employed, As a result, rapid treatment of skin exposed to toxic substances can be accomplished quickly and efficiently, in a variety of dispensing devices, such as wall-mounted shower head adapters, hand-held aerosol dispensers or hand-held shower devices.

In the foregoing description, certain terms and visual depictions are used to illustrate the preferred embodiment.

However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended claims.

The invention claimed is:

1. A zero leakage long term storage dispenser for delivering an aerosol containing decontamination fluid comprising;
    a hermetically sealed housing filled with decontamination fluid, an upper end of said housing having bellows type convolutions formed as part of an outer wall thereof;
    a dip tube within said housing having an upper end attached to a top wall of said housing and extending downwardly with a lower end of said dip tube open adjacent a bottom wall of said housing;
    a support tube within said housing attached to said bottom wall of said housing extending upwardly, an upper end of said support tube providing support for a propellant tank mounted above said support tube, the upper end of said support tube having a first hollow piercing needle extending upwardly, a pointed end of said first hollow piercing needle being aligned with and spaced from a sealed end of said propellant tank;
    a cap enclosing the upper end of said housing and threadably engaged with the outer wall of said housing below said bellows type convolutions;
    a discharge means mounted outside on said cap having a second hollow piercing needle extending down from said cap terminating above said top wall of said housing and aligned with said dip tube so that rotation of said cap will cause said second hollow piercing needle to penetrate said top wall of said housing and couple with said dip tube, wherein further rotation of said cap causing said first hollow piercing needle to pierce the sealed end of said propellant tank releasing propellant directly into said housing for driving said decontamination fluid up through said dip tube and out through said second hollow piercing needle and through said discharge means.

2. The long term storage dispenser of claim 1 in which said propellant tank is spring mounted within a frame attached to said support tube so that said propellant tank is movable with respect to said support tube.

3. The long term storage dispenser of claim 1 in which said propellant tank includes a discharge pressure regulator for resealing said propellant tank when desired discharge pressure inside said housing has been reached, said regulator metering propellant into said housing to maintain pressure.

4. The long term storage dispenser of claim 3 in which the top wall of said housing has a rupture disk and said cap has venting holes to prevent an explosion in the event of a regulator failure.

5. The long term storage dispenser as in claim 1 wherein said housing further comprises:
    a user-identifiable label for identifying the type of exposure to be washed from the skin of the user with contents of said housing.

6. The long term storage dispenser of claim 5 having a frangible tamper evident tape wrap to insure integrity of said dispenser.

7. The long term storage dispenser of claim 1 in which said discharge means is a combination of a nozzle with an attached valve.

8. The long term storage dispenser of claim 1 in which said discharge means is a hose with one end connected to said cap and an opposite end having a lever operated discharge valve and nozzle for directing flow of said decontamination fluid.

9. An aerosol dispenser for cleansing of skin exposed to toxic substances, comprising:
    a hermetically sealed housing containing decontamination fluid for long term zero leakage storage;
    an activator cap mounted on said housing having a first piercing member for penetrating said housing upon twisting of said activator cap to allow dispensing of said decontamination fluid; and
    said housing having means for pressurizing the interior of said housing upon continued twisting of said activator cap for causing the dispensing of said decontamination fluid.

10. The dispenser as in claim 9 wherein said housing has a dip tube attached to a top of said housing for directing decontamination fluid to an opening created by said piercing member;
    wherein said pressurizing means comprises a high-pressure propellant tank within said housing;
    wherein a second piercing member is provided to release contents of said propellant tank upon further twisting of said activator cap; and
    said first piercing member communicating with discharge means attached to said activator cap for directing flow of said decontamination fluid leaving said housing.

11. The dispenser as in claim 9 wherein said aerosol dispenser further comprises:
    a user-identifiable label for identifying the type of exposure to be washed from the skin of the user with contents of said aerosol dispenser.

* * * * *